(12) United States Patent
Wang et al.

(10) Patent No.: US 9,874,544 B2
(45) Date of Patent: Jan. 23, 2018

(54) GAS SENSOR

(71) Applicants: LITE-ON OPTO TECHNOLOGY (CHANGZHOU) CO., LTD., Changzhou, Jiangsu (CN); LITE-ON TECHNOLOGY CORPORATION, Taipei (TW)

(72) Inventors: Chiou-yueh Wang, New Taipei (TW); Shih-Chang Hsu, Taipei (TW)

(73) Assignees: LITE-ON OPTO TECHNOLOGY (CHANGZHOU) CO., LTD., Changzhou, Jiangsu Province (CN); LITE-ON TECHNOLOGY CORPORATION, Taipei (TW)

( * ) Notice: Subject to any disclaimer, the term of this patent is extended or adjusted under 35 U.S.C. 154(b) by 52 days.

(21) Appl. No.: 15/182,025

(22) Filed: Jun. 14, 2016

(65) Prior Publication Data
US 2017/0254779 A1    Sep. 7, 2017

(30) Foreign Application Priority Data

Mar. 7, 2016    (CN) .......................... 2016 1 0129086

(51) Int. Cl.
*G01N 27/62*    (2006.01)
*G01N 33/00*    (2006.01)
(Continued)

(52) U.S. Cl.
CPC ......... *G01N 27/628* (2013.01); *G01N 27/407* (2013.01); *G01N 27/626* (2013.01); *G01N 33/0009* (2013.01); *G01N 27/30* (2013.01)

(58) Field of Classification Search
CPC ...... G01N 27/00; G01N 27/62; G01N 27/626; G01N 27/628; G01N 27/26; G01N 27/30; G01N 27/304; G01N 27/404; G01N 27/4045; G01N 27/407; G01N 27/4071; G01N 27/409; G01N 27/4141;
(Continued)

(56) References Cited

U.S. PATENT DOCUMENTS 4,914,720 A * 4/1990 Knodle ................ A61B 5/0836
250/252.1
5,596,314 A * 1/1997 Goldstein ............ G08B 17/103
340/628

(Continued)

*Primary Examiner* — Hoai-An D Nguyen
(74) *Attorney, Agent, or Firm* — Li & Cai Intellectual Property (USA) Office

(57) ABSTRACT

A gas sensor includes a base, an insulating layer, two sensing electrodes, a heating layer, a gas-sensing material, and an exciting light source. A thru-hole is formed on the base, the insulating layer is disposed on the base to cover the thru-hole, and a portion of the insulating layer corresponding to the thru-hole is defined as an element area. Each sensing electrode disposed on the insulating layer has a sensing segment disposed on the element area and a sensing pad disposed outside the element area. The heating layer disposed on the insulating layer has a heating segment disposed on the element area and two heating pads disposed outside the element area. The gas-sensing material is disposed on the element area and covers the sensing segments and the heating segment. The exciting light source is arranged in the thru-hole and is configured to emit light toward the gas-sensing material.

19 Claims, 6 Drawing Sheets

(51) Int. Cl.
*G01N 27/407* (2006.01)
*G01N 27/30* (2006.01)

(58) Field of Classification Search
CPC ........... G01N 33/0009; G01N 33/0039; G01N 33/0004; G01N 33/0042; G01N 33/497
USPC ........ 324/459, 464; 204/400, 421, 424, 426, 204/431, 433; 205/784; 73/23.2
See application file for complete search history.

(56) References Cited

U.S. PATENT DOCUMENTS

| | | | | |
|---|---|---|---|---|
| 7,068,055 | B2* | 6/2006 | Hiroki | G01R 31/302 324/762.09 |
| 2005/0285039 | A1* | 12/2005 | Ludwig | G01N 21/3504 250/338.1 |
| 2006/0210237 | A1* | 9/2006 | Soeta | H01L 23/49816 385/147 |
| 2009/0151429 | A1* | 6/2009 | Jun | G01N 33/0027 73/31.06 |
| 2009/0312954 | A1* | 12/2009 | Utriainen | G01N 27/128 702/23 |
| 2012/0138459 | A1* | 6/2012 | Chen | G01N 27/127 204/424 |
| 2013/0075255 | A1* | 3/2013 | Moon | G01N 27/18 204/427 |
| 2017/0234821 | A1* | 8/2017 | Lee | H01L 45/00 257/414 |

* cited by examiner

GAS SENSOR

BACKGROUND OF THE INVENTION

1. Field of the Invention

The instant invention relates to a sensor; in particular, to a gas sensor having an exciting light source.

2. Description of Related Art

The conventional gas sensor is operated to heat a gas-sensing material by using a heater for ionizing a detected gas such that an electrical signal of the gas-sensing material is accordingly changed, and concentration of the detected gas can be obtained by the conventional gas sensor. However, heat generated from the heater of the conventional gas sensor is easily dissipated. Therefore, the heater must be operated at a higher power in order to maintain a predetermined high-temperature condition.

SUMMARY OF THE INVENTION

The instant disclosure provides a gas sensor for effectively solving the above problems generated from the conventional gas sensor.

In summary, an element area of the gas sensor in the instant disclosure is arranged corresponding to a thru-hole of a base, so that heat generated from the heating layer can be slowly transmitted to the base due to the thru-hole of the base, thereby reducing the heat-dissipation rate. Moreover, the exciting light source in the instant disclosure is arranged inside the thru-hole to minimize the size of the gas sensor, and the exciting light source is configured to excite the gas-sensing material for increasing sensitivity of the gas-sensing material and reducing heat supplied from the heating layer.

In order to further appreciate the characteristics and technical contents of the instant invention, references are hereunder made to the detailed descriptions and appended drawings in connection with the instant invention. However, the appended drawings are merely shown for exemplary purposes, rather than being used to restrict the scope of the instant invention.

DETAILED DESCRIPTION OF THE PREFERRED EMBODIMENTS

First Embodiment

Figure 1:
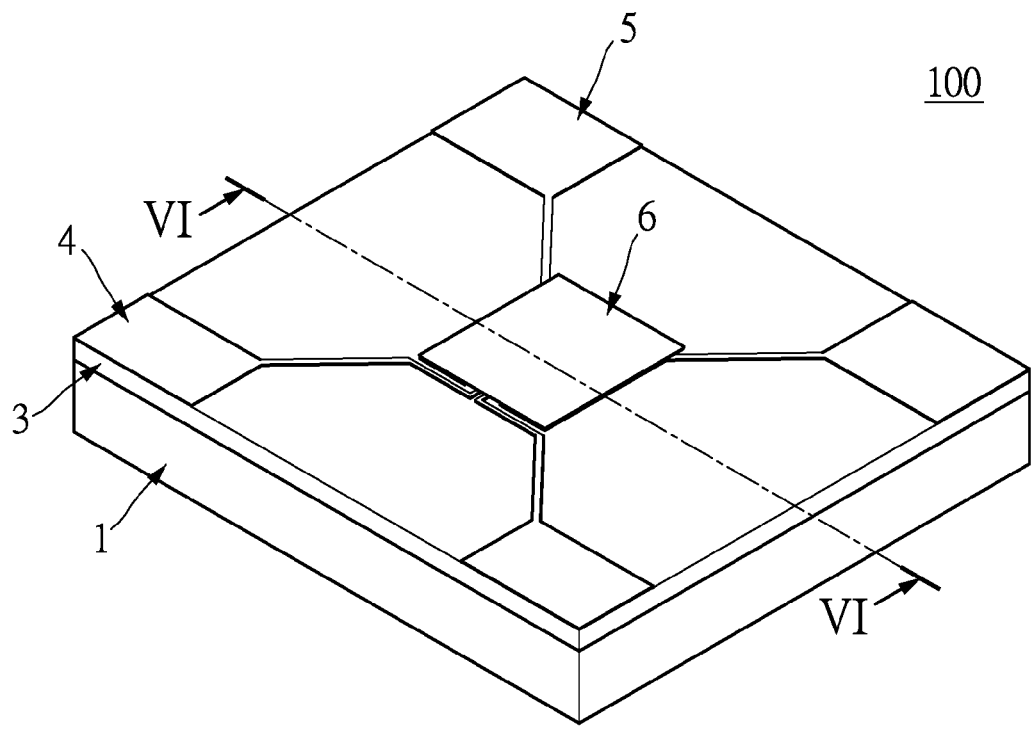
FIG. 1 is a perspective view showing a gas sensor according to a first embodiment of the instant disclosure.
Figure 2:
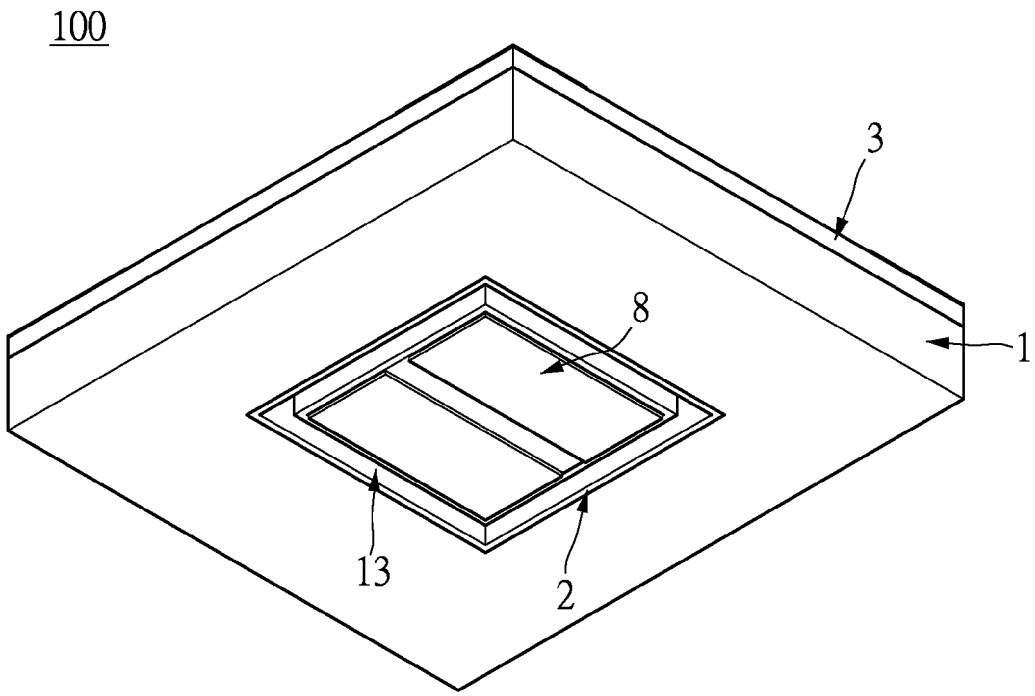
FIG. 2 is an another perspective view of FIG. 1.
Figure 3:
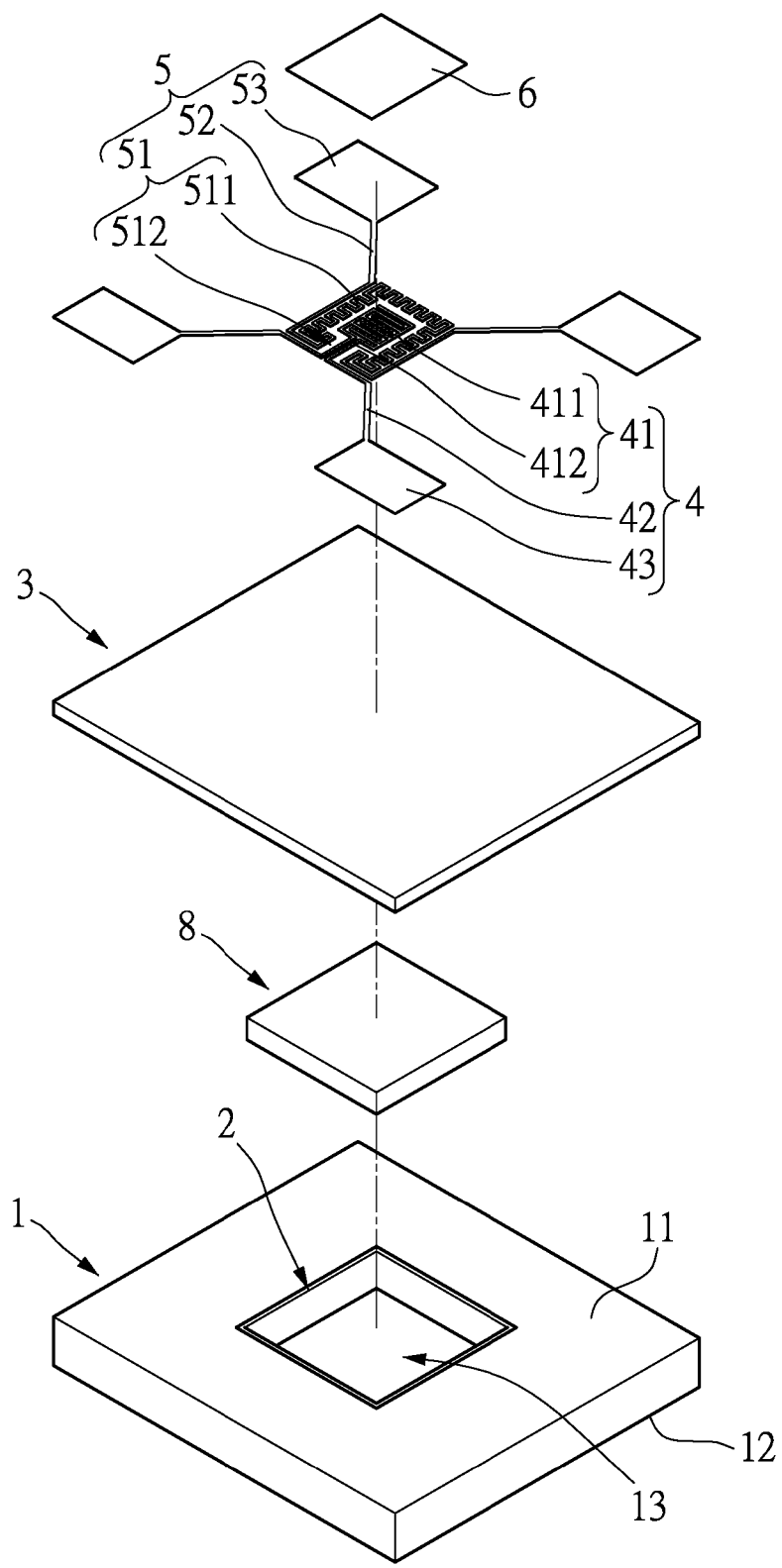
FIG. 3 is an exploded view of FIG. 1.
Figure 4:
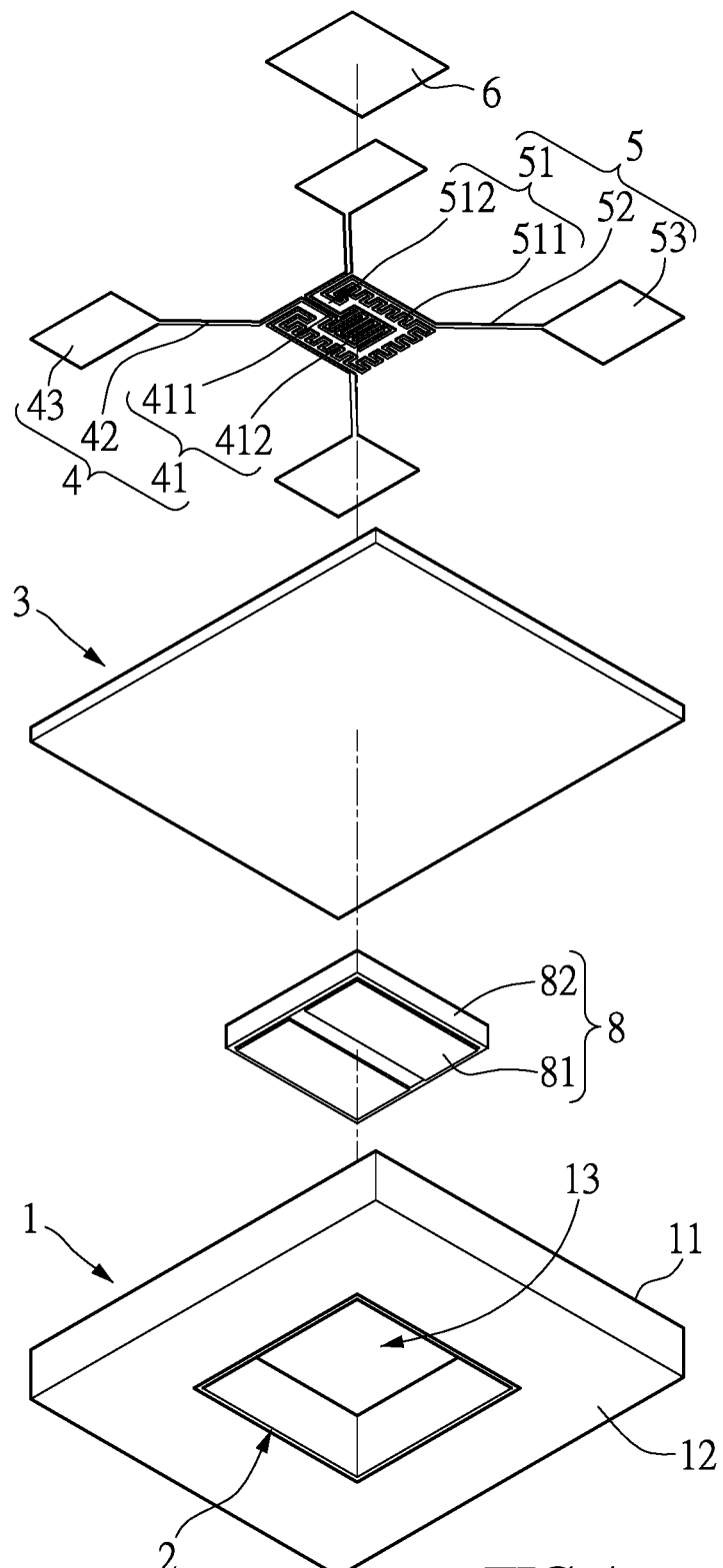
FIG. 4 is an exploded view of FIG. 2.
Figure 5:
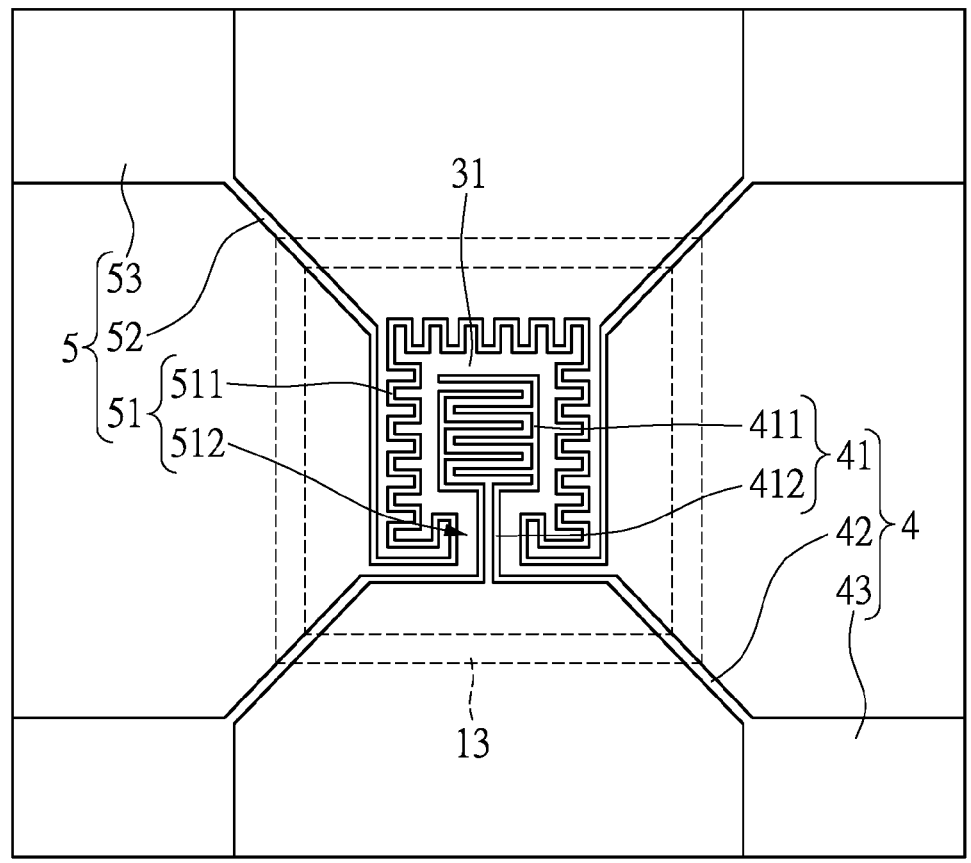
FIG. 5 is a top view of the gas sensor of the instant disclosure as the gas-sensing material is omitted.
Figure 6:
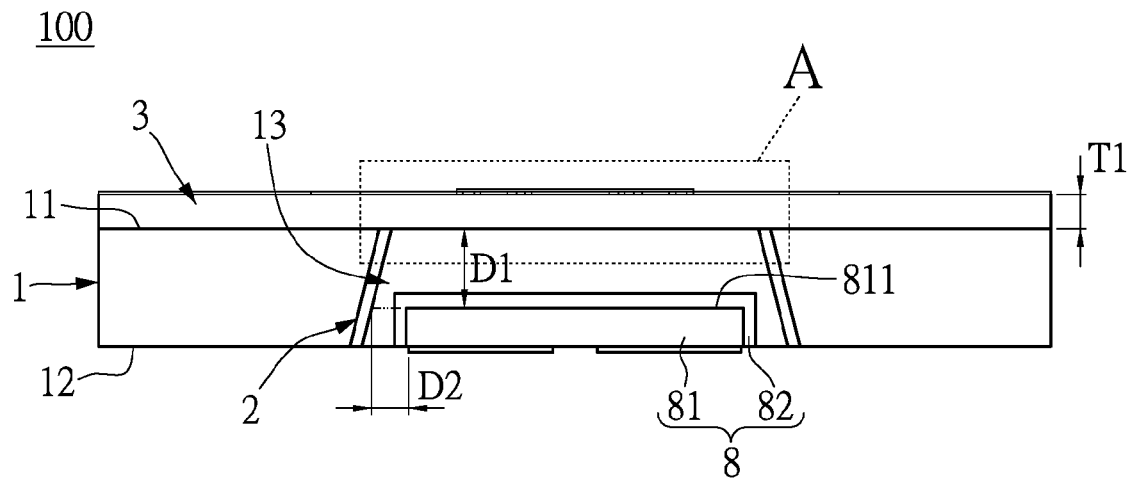
FIG. 6 is a cross-sectional view of FIG. 1 along a line VI-VI.
Figure 7:
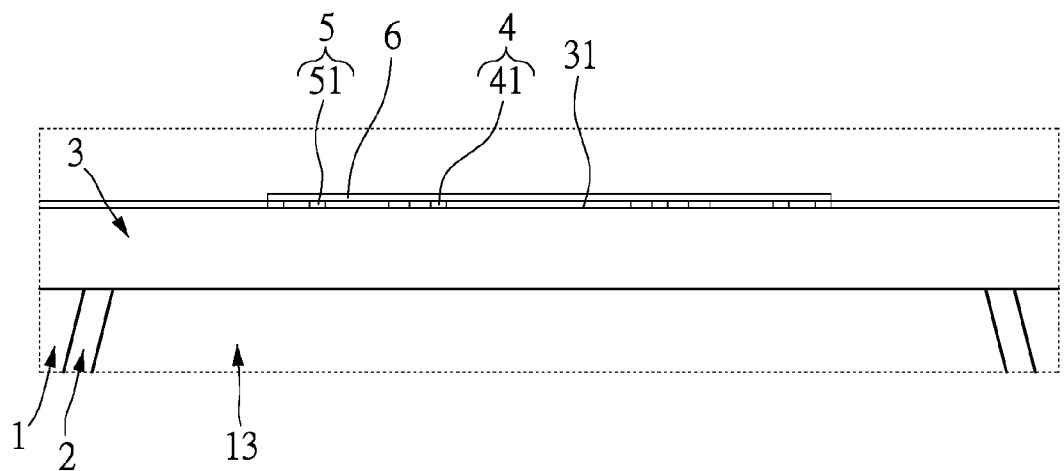
FIG. 7 is an enlarged view of FIG. 6 showing the A portion.

Please refer to FIGS. 1 through 8, which show a first embodiment of the instant disclosure. References are hereunder made to the detailed descriptions and appended drawings in connection with the instant invention. However, the appended drawings are merely shown for exemplary purposes, rather than being used to restrict the scope of the instant invention.

Please refer to FIGS. 1 through 4, which show a gas sensor 100 (e.g., a MEMS gas sensor) used for sensing a detected gas (e.g., carbon monoxide, ethanol, or poison gas). The gas sensor 100 includes a base 1, a reflecting layer 2, an insulating layer 3, two sensing electrodes 4, a heating layer 5, a gas-sensing material 6, and an exciting light source 8.

Please refer to FIGS. 4 through 7. The base 1 in the instant embodiment is approximately a bulk and is made of silicon. The base 1 has a top surface 11 and a bottom surface 12 opposing to the top surface 11, and the top surface 11 and the bottom surface 12 each have an approximately square shape. A thru-hole 13 penetrates through a center portion of the base 1 from the top surface 11 to the bottom surface 12 so as to form an inner wall of the base 1. A top portion of the thru-hole 13 corresponding to the top surface 11 has a smaller square shape, and a bottom portion of the thru-hole 13 corresponding to the bottom surface 12 has a bigger square shape. That is to say, the thru-hole 13 is formed as a truncated pyramid.

The reflecting layer 2 is formed on the inner wall of the base 1. A light reflectivity of the reflecting layer 2 corresponding to light emitted from the exciting light source 8 is greater than 70%, and the reflecting layer 2 is made of silica, boron nitride, alumina, aluminum, silver, or gold, but the reflecting layer 2 is not limited thereto.

The insulating layer 3 is disposed on the top surface 11 of the base 1 and entirely covers the thru-hole 13. The periphery edge of the insulating layer 3 is aligned with the periphery edge of the base 1. A portion of the insulating layer 3 corresponding to the thru-hole 13 is defined as an element area 31. Specifically, a portion of the insulating layer 3 smaller than the top portion of the thru-hole 13 can be the element area 31, or a portion of the insulating layer 3 entirely covering the thru-hole 13 can be the element area 31. The insulating layer 3 has a silica layer and a silicon nitride layer stacked on the silica layer. A thickness of the silica layer is approximately 500 nm~1500 nm, and a thickness T of the silicon nitride layer is approximately 50 nm~250 nm. Or, the insulating layer 3 is composed of a silicon nitride layer having a thickness T of 50 nm~250 nm.

The two sensing electrodes 4 are made of gold, and are spaced apart from each other and arranged on the insulating layer 3. Each of the sensing electrodes 4 has a sensing segment 41, a connecting segment 42, and an electrode pad 43. The two sensing segments 41 are disposed on the element area 31, the two electrode pads 43 are disposed outside the element area 31 and are distributed at two adjacent corners of four corners of the insulating layer 3, and the two connecting segments 42 respectively connect the two sensing segments 41 to the two electrode pads 43.

The heating layer 5 made of gold or a transparent electrode (e.g., Indium Tin Oxide, ITO) is disposed on the insulating layer 3. When the heating layer 5 and the two sensing electrodes 4 are formed by the same material, the heating layer 5 and the two sensing electrode 4 can be together formed on the insulating layer 3 in one process. The heating layer 5 has a heating segment 51, two externally connecting segments 52, and two heating pads 53. The heating segment 51 is disposed on the element area 31, and the two heating pads 53 are disposed outside the element area 31 and are distributed at the other two corners of the four corners of the insulating layer 3. That is to say, the two electrode pads 43 and the two heating pads 53 are respectively distributed at the four corners of the insulating layer 3. The two externally connecting segments 52 respectively connect the two heating pads 53 to the heating segment 51.

Specifically, each of the two sensing segments 41 has a finger portion 411 and an extending portion 412 connected to the finger portion 411. The two finger portions 411 are interdigitated with each other and are disposed on the center portion of the element area 31. The heating segment 51 has a plurality of head-to-tail U-shaped portions 511, two ends of each U-shaped portion 511 are respectively connected to an ends of two adjacent U-shaped portions 511, and each U-shaped portion 511 and the adjacent U-shaped portion 511 are arranged to face in two different directions. The plurality of head-to-tail U-shaped portions 511 are arranged around the two finger portions 411 to define a notch 512. In other words, the plurality of head-to-tail U-shaped portions 511 are arranged in a U shape to form the notch 512. The two extending portions 412 are respectively extended from the two finger portions 411 to the two connecting segments 42 through the notch 512.

The gas-sensing material 6 having an approximately square shape is disposed on the element area 31. The gas-sensing material 6 at least covers the two sensing segments 41, and the gas-sensing material 6 in the instant embodiment covers the two sensing segments 41 and the heating segment 51. In other words, the gas-sensing material 6 is disposed on the two sensing segments 41 and the heating segment 51. In addition, the gas-sensing material 6 can be a circular shape, oval shape, rectangular shape, or other shapes. The gas-sensing material 6 is a metal oxide semiconductor (MOS) material having zinc oxide (ZnO), aluminum-doped zinc oxide (Al: ZnO), tin dioxide ($SnO_2$), tungsten oxide, titanium oxide, indium oxide, iron oxide, copper oxide, nickel oxide, or cobalt oxide, but the gas-sensing material 6 is not limited thereto.

The exciting light source 8 is at least partially arranged in the thru-hole 13 of the base 1. The exciting light source 8 is configured to emit light toward the gas-sensing material 6 arranged on the element area 31 such that an electrical signal of the gas-sensing material 6 can be generated. The electrical signal can be a voltage signal, a current signal, or a resistance signal. The exciting light source 8 in the instant embodiment has a LED die 81 and a protecting layer 82 packaging on a light emitting surface of the LED die 81. A viewing angle of the LED die 81 having the protecting layer 82 is smaller than that of the LED die 81 without the protecting layer 82. The protecting layer 82 is made of epoxy resin or silicone resin. The LED die 81 in the instant embodiment is a flip-chip, but is not limited thereto.

Specifically, a distance D1 between a quantum well 811 of the LED die 81 and the gas-sensing material 6 is approximately 2 μm~1000 μm, and a distance D2 between the LED die 81 and the inner wall of the base 1 is greater than 0.1 mm. Moreover, an energy band gap of the gas-sensing material 6 is defined as E, and a wavelength of light emitted from the exciting light source 8 is defined as λ. The relative parameters of E and λ satisfy the following formula: $1240/E \times 87\% < \lambda < 1240/E \times 113\%$.

If the gas-sensing material 6 is made of $ZrO_2$ having a higher energy band gap (E) of 5.0 eV, a minimum λ value of 215 nm is obtained by substituting E=5.0 eV into the above formula. If the gas-sensing material 6 is made of CdTe having a lower energy band gap (E) of 1.4 eV, a maximum λ value of 1000 nm is obtained by substituting E=1.4 eV into the above formula. Accordingly, the wavelength of light emitted from the exciting light source 8 is 215 nm~1000 nm.

Figure 8:
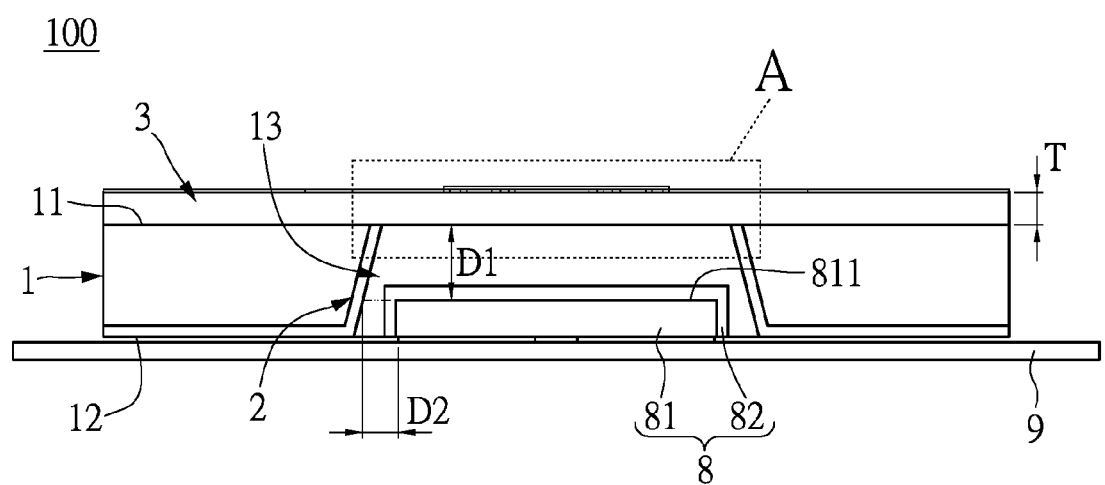
FIG. 8 is a cross-sectional view showing the gas sensor provided with a submount.

In addition, as shown in FIG. 8, the gas sensor 100 further comprises a submount 9. The exciting light source 8 is fixed on the submount 9, and the submount 9 corporates with the base 1 having the thru-hole 13 to form a space, the space is filled with air or is in a vacuum mode.

The construction of the gas sensor 100 has been disclosed in the above description. Accordingly, heat, which is generated from the heating layer 5 arranged on the element area 31, can be slowly transmitted to the base 1 due to the thru-hole 13 of the base 1, thereby reducing the heat-dissipation rate. Moreover, the exciting light source 8 is arranged inside the thru-hole 13 to minimize the size of the gas sensor 100, and the gas-sensing material 6 can be excited by the exciting light source 8 for increasing sensitivity of the gas-sensing material 6 and reducing heat supplied from the heating layer 5.

The following description discloses three different experiments to realize the sensitivity of the gas sensor 100 in different conditions. The sensitivity of the gas sensor 100 is defined as $(R_{air}-R_{gas})/R_{air}$. $R_{air}$ is a resistance of the gas-sensing material 6 measured in a normal air, and $R_{gas}$ is a resistance of the gas-sensing material 6 measured in a detected gas.

(First Experiment)

The treatment group is the gas sensor 100 of the instant embodiment, and light emitted from the exciting light source 8 has a wavelength of 365 nm. The control group is a gas sensor provided without any exciting light source 8. The fixed parameters are shown as below. The gas-sensing material 6 is made of aluminum-doped zinc oxide having an area of 0.16 $mm^2$, a current of 150 mA is applied to the exciting light source 8, and the detected gas adapts alcohol having a concentration of 53 ppm. The varied parameter is a voltage of 0~2 V supplied to the heating layer 5.

The result of the first experiment is shown in the following chart. According to this chart, the gas-sensing material 6 can be provided with better sensitivity by using the exciting light source 8. Moreover, compared to the gas sensor provided without any exciting light source 8, the gas sensor 100 of the instant embodiment can use the exciting light source 8 to reduce the heating temperature of the heating layer 5.

| heating layer | | | | 365 nm LED | no LED |
|---|---|---|---|---|---|
| voltage (V) | current (mA) | power (mW) | temperature (° C.) | sensitivity (%) | sensitivity (%) |
| 0 | 0 | 0 | — | — | 0 |
| 1.00 | 27 | 27 | 88 | 9.3 | 0.25 |
| 1.25 | 36 | 45 | 135 | 13 | 0.5 |
| 1.50 | 43 | 64.5 | 182 | 21 | 3 |
| 1.75 | 50 | 87.5 | 242 | 23 | 6 |
| 2.00 | 53 | 106 | 307 | 22 | 12 |

(Second Experiment)

The treatment group is the gas sensor 100 of the instant embodiment, and light emitted from the exciting light source 8 has a wavelength of 365 nm. The fixed parameters are shown as below. The gas-sensing material 6 is made of aluminum-doped zinc oxide and has an area of 0.16 $mm^2$, a voltage of 1.75 V is applied to the heating layer 5, and the detected gas adapts alcohol having a concentration of 53 ppm. The varied parameter is a current of 0~150 mA supplied to the exciting light source 8.

The result of the second experiment is shown as the following chart. According to this chart, when current supplied to the exciting light source 8 of the gas sensor 100 is increased, the sensitivity of the gas-sensing material 6 is increased.

| 365 nm LED | | | |
|---|---|---|---|
| current (mA) | voltage (V) | power (mW) | sensitivity (%) |
| 0 | 0 | 0 | 6.0 |
| 10 | 3.12 | 31 | 12.8 |
| 25 | 3.24 | 81 | 15.8 |
| 50 | 3.37 | 168 | 19.6 |
| 100 | 3.63 | 363 | 21.8 |
| 150 | 3.88 | 582 | 23.0 |

(Third Experiment)

The treatment group is the gas sensor 100 of the instant embodiment, and light emitted from the exciting light source 8 has a wavelength of 365 nm, 405 nm, 410 nm, or 448 nm. The fixed parameters are shown as below. The gas-sensing material 6 is made of aluminum-doped zinc oxide and has an area of 0.16 mm$^2$, a voltage of 1.75 V is applied to the heating layer 5, and the detected gas adapts alcohol having a concentration of 53 ppm. The varied parameter is a current of 0, 150 mA, or 500 mA supplied to the exciting light source 8.

The result of the third experiment is shown in the following chart. According to this chart, when current supplied to the exciting light source 8 of the gas sensor 100 is increased, the sensitivity of the gas-sensing material 6 is increased. However, when light emitted from the exciting light source 8 has a wavelength lager than 448 nm, the sensitivity of the gas-sensing material 6 is slightly increased when current supplied to the exciting light source 8 of the gas sensor 100 is increased.

Specifically, the energy band gap (E) of the aluminum-doped zinc oxide is 3.4 eV, so $\lambda$=1240/3.4=365 nm and 410 nm/365 nm=113%. Thus, the preferable maximum $\lambda$ value (i.e., $\lambda$<1240/E×113%) can be obtained based on the result of the third experiment. Similarly, the preferable minimum $\lambda$ value (i.e., 1240/E×87%<$\lambda$) can be obtained based on an experiment similar to the third experiment.

| wavelength (nm) | 0 mA sensitivity (%) | 150 mA sensitivity (%) | 500 mA sensitivity (%) |
|---|---|---|---|
| 365 | 12 | 24.5 | 30.8 |
| 405 | 14 | 17 | 19.6 |
| 410 | 12.5 | 17 | 20 |
| 448 | 13 | 13.5 | 14.5 |

Second Embodiment

Figure 9:
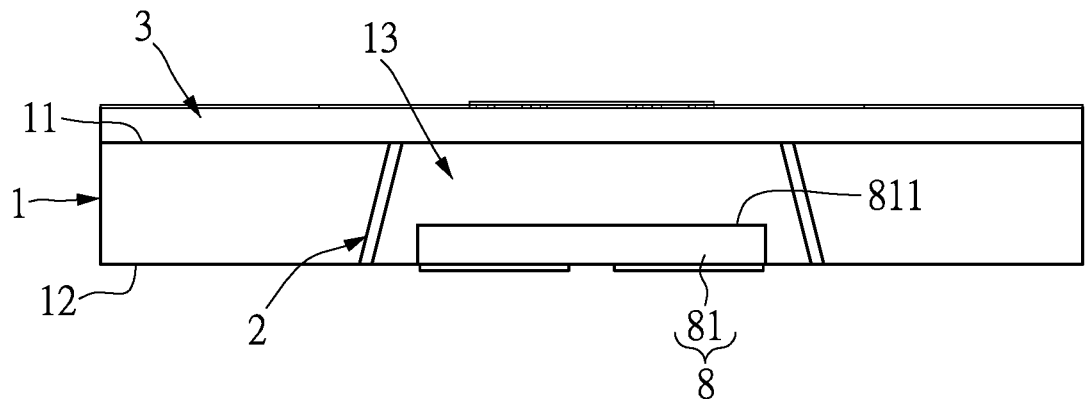
FIG. 9 is a cross-sectional view showing a gas sensor according to a second embodiment of the instant disclosure.

Please refer to the FIG. 9, which shows a second embodiment of the instant disclosure. The second embodiment is similar to the first embodiment. The main different feature of the two embodiments is that the exciting light source 8 in the instant embodiment is the bare LED die 81. That is to say, the exciting light source 8 in the instant embodiment is the LED die 81 provided without the protecting layer 82. Thus, based on the two embodiments, the protecting layer 82 can be selectively disposed on the bare LED die 81 for achieving the user's demand.

Third Embodiment

Figure 10:
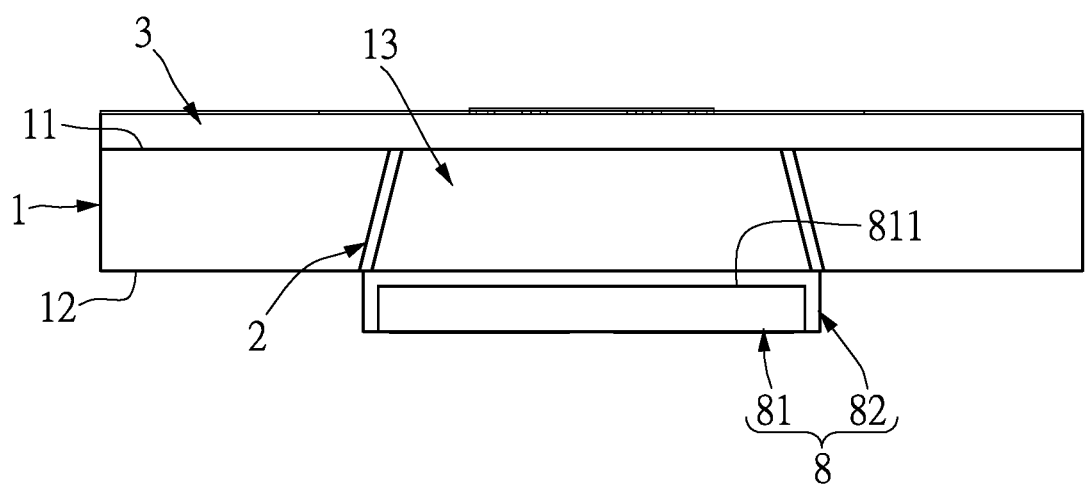
FIG. 10 is a cross-sectional view showing a gas sensor according to a third embodiment of the instant disclosure.

Please refer to the FIG. 10, which shows a third embodiment of the instant disclosure. The third embodiment is similar to the first embodiment and the second embodiment. A main different feature is that the exciting light source 8 of the instant embodiment is arranged outside the thru-hole 13 of the base 1.

The descriptions illustrated supra set forth simply the preferred embodiments of the instant invention; however, the characteristics of the instant invention are by no means restricted thereto. All changes, alterations, or modifications conveniently considered by those skilled in the art are deemed to be encompassed within the scope of the instant invention delineated by the following claims.

What is claimed is:

1. A gas sensor, comprising:
   a base including a top surface and a bottom surface opposing to the top surface, a thru-hole penetrating through the base from the top surface to the bottom surface so as to form an inner wall of the base;
   an insulating layer disposed on the top surface of the base and entirely covering the thru-hole, wherein a portion of the insulating layer corresponding to the thru-hole is defined as an element area;
   two sensing electrodes arranged on the insulating layer;
   a heating layer disposed on the insulating layer;
   a gas-sensing material disposed on the element area of the insulating layer; and
   an exciting light source arranged in the thru-hole of the base, wherein the exciting light source is configured to emit light toward the gas-sensing material.

2. The gas sensor as claimed in claim 1, wherein the insulating layer has a silica layer and a silicon nitride layer stacked on the silica layer, a thickness of the silica layer is approximately 500 nm~1500 nm, and a thickness of the silicon nitride layer is approximately 50 nm~250 nm.

3. The gas sensor as claimed in claim 1, wherein the insulating layer is a silicon nitride layer having a thickness of 50 nm~250 nm.

4. The gas sensor as claimed in claim 1, wherein the thru-hole is formed as a truncated pyramid.

5. The gas sensor as claimed in claim 1, wherein the gas-sensing material is a metal oxide semiconductor (MOS) material having zinc oxide (ZnO), aluminum-doped zinc oxide (Al: ZnO), tin dioxide ($SnO_2$), tungsten oxide, titanium oxide, indium oxide, iron oxide, copper oxide, nickel oxide, or cobalt oxide.

6. The gas sensor as claimed in claim 1, further comprising a reflecting layer formed on the inner wall of the base, wherein a light reflectivity of the reflecting layer corresponding to light emitted from the exciting light source is greater than 70%.

7. The gas sensor as claimed in claim 6, wherein the reflecting layer is made of silica, boron nitride, alumina, aluminum, silver, or gold.

8. The gas sensor as claimed in claim 1, wherein the exciting light source is a LED die, a protecting layer is selectively disposed on a light emitting surface of the LED die, and a viewing angle of the LED die having the protecting layer is smaller than that of the LED die without the protecting layer.

9. The gas sensor as claimed in claim 8, wherein a distance between a quantum well of the LED die and the gas-sensing material is approximately 2 μm~1000 μm.

10. The gas sensor as claimed in claim 8, wherein a distance between the LED die and the inner wall of the base is greater than 0.1 mm.

11. The gas sensor as claimed in claim 1, further comprising a submount, wherein the exciting light source is disposed on the submount, and a space formed by the submount and the base having the thru-hole is filled with air.

12. The gas sensor as claimed in claim 1, further comprising a submount, wherein the exciting light source is disposed on the submount, and the submount corporates with the base having the thru-hole to form a vacuum space.

13. The gas sensor as claimed in claim 1, wherein an energy band gap of the gas-sensing material is defined as E, a wavelength of light emitted from the exciting light source is defined as $\lambda$, the energy band gap of the gas-sensing material and the wavelength of light satisfy the following formula: $1240/E \times 87\% < \lambda < 1240/E \times 113\%$.

14. The gas sensor as claimed in claim 1, wherein each of the two sensing electrodes has a sensing segment, an electrode pad, and a connecting segment connecting the sensing segment and the electrode pad, the sensing segment of each of the two sensing electrodes is disposed on the element area, and the electrode pad of each of the two sensing electrodes is disposed outside the element area.

15. The gas sensor as claimed in claim 14, wherein the heating layer has a heating segment, two heating pads, and two externally connecting segments respectively connecting the two heating pads to the heating segment, the heating segment is disposed on the element area, and the two heating pads are disposed outside the element area.

16. The gas sensor as claimed in claim 14, wherein the gas-sensing material at least covers the two sensing segments.

17. The gas sensor as claimed in claim 14, wherein the gas-sensing material covers the two sensing segments and the heating segment.

18. The gas sensor as claimed in claim 15, wherein each of the two sensing segments has a finger portion and an extending portion connected to the finger portion, and the two finger portions are interdigitated with each other, the heating segment has a plurality of head-to-tail U-shaped portions, the U-shaped portions are arranged around the two finger portions to define a notch, and the two extending portions are respectively extended from the two finger portions to the two connecting segments through the notch.

19. The gas sensor as claimed in claim 18, wherein two ends of each U-shaped portion are respectively connected to an ends of two adjacent U-shaped portions, and each U-shaped portion and the adjacent U-shaped portion are arranged to face in two different directions.

* * * * *